(12) United States Patent
Yu et al.

(10) Patent No.: US 6,656,708 B1
(45) Date of Patent: Dec. 2, 2003

(54) HUMAN GROWTH DIFFERENTIATION FACTOR ENCODING SEQUENCE AND POLYPEPTIDE ENCODED BY SUCH DNA SEQUENCE AND PRODUCING METHOD THEREOF

(75) Inventors: Long Yu, Handan Road 220, Institute of Genetics, Fudan University, Shanghai (CN), 200433; Honglai Zhang, Shanghai (CN); Qiang Fu, Shanghai (CN); Fangyan Dai, Shanghai (CN); Shouyuan Zhao, Shanghai (CN)

(73) Assignee: Long Yu, Shanghai (CN)

( * ) Notice: Subject to any disclaimer, the term of this patent is extended or adjusted under 35 U.S.C. 154(b) by 0 days.

(21) Appl. No.: 09/787,351

(22) PCT Filed: Sep. 6, 1999

(86) PCT No.: PCT/CN99/00138

§ 371 (c)(1),
(2), (4) Date: Mar. 16, 2001

(87) PCT Pub. No.: WO00/17350

PCT Pub. Date: Mar. 30, 2000

(30) Foreign Application Priority Data

Sep. 22, 1998 (CN) ............................................. 98119759

(51) Int. Cl.[7] ............................ C12P 21/00; C12N 1/21; C12N 15/12; C12N 15/70; C07K 14/51

(52) U.S. Cl. ..................... 435/69.4; 435/69.1; 435/325; 435/252.3; 435/252.33; 435/320.1; 530/350; 536/23.5; 536/23.51; 536/24.1

(58) Field of Search ............................... 435/69.4, 69.1, 435/325, 252.3, 320.1, 252.33; 530/350; 536/23.5, 23.51, 24.1

(56) References Cited

FOREIGN PATENT DOCUMENTS

WO WO94/15965 7/1994

OTHER PUBLICATIONS

McPherron et al., "GDF–3 and GDF–9: two new members of the transforming growth factor–beta superfamily containing a novel pattern of cysteines," *Journal of Biological Chemistry*, vol. 268, No. 5, pp. 3444–3449 (1993).

Jones et al., "Isolation of Vgr–2, a novel member of the transforming growth factor–beta–related gene family," *Molecular Endocrinology*, vol. 6, No. 11, pp. 1961–1968 (1992).

Caricasole et al., "Human growth–differentiation factor 3 (hGDF3): developmental regulation in human teratocarcinoma cell lines and expression in primary testicular germ cell tumours," *Oncogene*, vol. 16, pp. 95–103 (1998).

Grande, J.P., "Role of Transforming Growth Factor–β in Tissue Injury and Repair," *P.S.E.B.M.*, vol. 214, pp. 27–40 (1997).

Alevizopoulos et al., "Transforming growth factor–β: the breaking open of a black box," *BioEssays*, Vol 19, No. 7, pp. 581–591 (1997).

Cox et al., "Transforming Growth Factor–β," *Clinical Immunology and Immunopathology*, vol. 83, No. 1, pp. 25–30 (1997).

*Primary Examiner*—David S. Romeo
(74) *Attorney, Agent, or Firm*—Merchant & Gould, P.C.

(57) ABSTRACT

The invention provides a cDNA sequence of a new human growth differentiation factor (hGDF3-2). The protein encoded by such sequence is a splice variant of hGDF3. The present invention also relates to peptides encoded by the nucleotide sequences, to uses of these polynucleotides and polypeptides, and methods for producing the said polynucleotides and polypeptides.

8 Claims, 1 Drawing Sheet

```
hGDF3-2   MLRFLPDLAFSFLLI-LALGQAVQFQEYVFLQFLGLDKAPSPHKFQPVPY         49
hGDF3     M------------------------------------------------          1
GDF3      MQPYQRLLALGFLLLTLPWGQTSEFQDSDLLQFLGLEKAPSPHRFQPVPR         50
                                          * hGDF3-2   ILKKIFQDREAAATTGVSRDLCYVKELGVRGNVLRFLPDQGFFLYPKKIS         99
hGDF3     --KEISQDREAAATTGVSRDLCYVKELGVRGNVLRFLPDQGFFLYPKKIS         49
GDF3      VLRKIIRAREAAAASGASQDLCYVKELGVRGNLLQLLPDQGFFLNTQKPF        100
          ..*..*****..*.*.************.*..*******...* hGDF3-2   QASSCLQKLLYFNLSAIKEREQLTLAQL-VDLGPNSYYNLGPELELALFL        148
hGDF3     QASSCLQKLLYFNLSAIKEREQLTLAQL-VDLGPNSYYNLGPELELALFL         98
GDF3      QDGSCLQKVLYFNLSAIKEKAKLTMAQLTLDLGPRSYYNLRPELVVALSV        150
          *..*****.**********...**.***.****.*****.***.**.

hGDF3-2   VQEPHVWRQTTPKPGKMFVLRSVPWPQGAVHFSLLDVAKDWNDNPRKNFG        198
hGDF3     VQEPHVWRQTTPKPGKMFVLRSVPWPQGAVHFSLLDVAKDWNDNPRKNFG        148
GDF3      VQDRGVWGRSHPKVGRLLFLRSVPGPQGQLQFNLQGALKDWSSNRLKNLD        200
          **..**..**.*...*****.***...*.*..***..*.**..

hGDF3-2   LFLEILVKENRDSGVNFQPEDTCARLRCSLHASLLVVTLNPDQCHPS-RK        247
hGDF3     LFLEILVKENRDSGVNFQPEDTCARLRCSLHASLLVVTLNPDQCHPS-RK        197
GDF3      LHLEILVKEDRYSRVTVQPENPCDPLLRSLHASLLVVTLNPKHCHPSSRK        250
          *.*******.*.*.***..*..*.*.*************..****.**

hGDF3-2   RRAAIPVPKLSCKNLCHRHQLFINFRDLGWHKWIIAPKGFMANYCHGECP        297
hGDF3     RRAAIPVPKLSCKNLCHRHQLFINFRDLGWHKWIIAPKGFMANYCHGECP        247
GDF3      RRAAISVPKGFCRNFCHRHQLFINFQDLGWHKWVIAPKGFMANYCHGECP        300
          ***.*..*.*.********.***.************** hGDF3-2   FSLTISLNSSNYAFMQALMHAVDPEIPQAVCIPTKLSPISMLYQDNNDNV        347
hGDF3     FSLTISLNSSNYAFMQALMHAVDPEIPQAVCIPTKLSPISMLYQDNNDNV        297
GDF3      FSMTTYLNSSNYAFMQALMHMADPKVPKAVCVPTKLSPISMLYQDSDKNV        350
          **.*.*.*************.**..*.***.*************...**

hGDF3-2   ILRHYEDMVVDECGCG                                          363
hGDF3     ILRHYEDMVVDECGCG                                          313
GDF3      ILRHYEDMVVDECGCG                                          366
          ****************
```

Fig. 1

HUMAN GROWTH DIFFERENTIATION FACTOR ENCODING SEQUENCE AND POLYPEPTIDE ENCODED BY SUCH DNA SEQUENCE AND PRODUCING METHOD THEREOF

FIELD OF INVENTION

This invention relates to the field of genetic engineering, and, in particular, relates to the nucleotide sequence of a novel human gene. More particularly, this invention relates to the cDNA sequence of a novel human Growth/Differentiation Factor (hGDF3-2), which is a splice variant of hGDF3. The invention also relates to the polypeptides encoded by the nucleotide sequence, the uses of these polynucleotides and polypeptides, and the methods for producing them.

PRIOR ART

Transforming Growth Factor-$\beta$ (TGF-$\beta$) was discovered about 15 years ago, using biochemical means. It is a protein with many biological regulatory activities. Shortly after the discovery, it was found that TGF-$\beta$ represented a group of growth factors with various functions. In different organisms, these factors exert important regulatory functions on cell growth, differentiation and tissue morphogenesis. (Handbook of Experimental Pharmacology, 1990, Vol.95, p419–475, Springer Verlag, Geidelberg). TGF-$\beta$, together with these related proteins, forms a superfamily named TFG-$\beta$ superfamily. Up to now, the TGF-$\beta$ superfamily has over 30 different members. There are four major families in the TGF-$\beta$ superfamily (Proc Soc Exp Biol Med, 1997, 214(1), 27–40), which are: (1) the Mullerian inhibitory substance (MIS) family—MIS regulates Mullerian duct regression in male embryos; (2) the inhibin/activin family—Inhibins block the follicle stimulating hormone (FSH) release by the pituitary cell, and activins stimulate FSH release; (3) Vg-related family, which includes bone morphogenic protein (BMP), dorsalin-1 (which regulates the differentiation of neural tube), growth/differentiation factor GDF-1, DPP, Vgl in the Xenopus and the murine homolog Vgr-1, etc.; (4) TGF-$\beta$ family, which includes five isoforms of TGF-$\beta$ (TGF-$\beta$ 1–5).

As a representative of this superfamily, TGF-$\beta$ has been extensively and intensively studied. The investigation indicates that TGF-$\beta$ is a strong endogenous mediators of tissue repair via their stimulatory effects on chemotaxis, angiogenesis, and extracellular matrix (ECM) deposition within the wound: environment. (Clin Immunol Immunopatol, 1997,83(1), 25–30). TGF-$\beta$ also regulates the growth and differentiation of various cells (Bioessays,1997, 19(7), 581–591), either positively or negatively. Most of the evidences suggest that TGF-$\beta$ exerts its regulatory effects at the G1 phase of cell cycle. Besides, it is reported that TGF-$\beta$ can induce cell death of some sensitive cell types, including hepatoma, myeloid, and osteoclast cells. In vitro experiments also show TGF-$\beta$ regulates the differentiation of various cell strains, though the mechanism is still unknown. The regulatory activity of TGF-$\beta$ on cell growth and differentiation naturally leads to considerations on the potential application in chemotherapy and cancer therapy. There have been considerable amount of reports concerning these topics (Clin Immunol Immunopathol, 1997, 83(1), 25–30; Bioessays, 1997, 19(7),581–591).

Members of TGF-$\beta$ family have been found in many species, e.g., Xenopus, fowl, mice, swine, bovine, etc. Human TGF-$\beta$ (–1,–2,–3) were cloned in the late 1980's. Among them, the sequencing of TGF-$\beta_1$, was finished by Derynck R et al. in 1985. (Nature, 1985, 316(6030), 701–705). By analyzing the sequence encoding TGF-$\beta_1$, they found that functional TGF-$\beta$ was produced by splicing a precursor that was much longer than the mature protein. Later, people found this phenomenon was common in TGF-$\beta$ superfamily. In 1988, the TGF-$\beta_2$ and TGF-$\beta_3$ nucleotide sequences were obtained by Madisen L et al. and Ten Dijke P et al., respectively. (Proc Natl Acad Sci USA, 1988, 85(13), 4715–4719; DNA, 1988, 7(1), 1–8). Sequence comparison showed the homology between TGF-$\beta_2$, TGF-$\beta_3$ and TGF-$\beta_1$ was 70%–80%.

Along with the steady improvements of gene cloning and sequencing techniques, more and more members of TGF-$\beta$ superfamily have been cloned since 1990. Alexandra. C reported in 1993 that they found a novel member of TGF-$\beta$ superfamily—murine Growth/Differentiation Factor 3, GDF-3 (J. Biol. Chem., 1993, 268(5), 3444–3449). The homology between GDF-3 and other members of the TGF-$\beta$ superfamily is not very high. But it still contains the unique conservative sequence of the TGF-$\beta$ superfamily. In particular, it lacks the fourth cystein of the seven conservative cysteins of the superfamily, indicating that it might have some particular property.

The homologue of GDF-3 in human was cloned in 1998 (Oncogene, 1998, 16, 95–103). This protein is highly homologous to the murine GDF-3, and thus named hGDF-3. Nevertheless, it is noteworthy that hGDF-3 is much shorter than GDF-3, mainly due to the lack of nearly 50 residues in the N-terminal. Moreover, two residues corresponding to residues 128 and 248 in the murine GDF-3 are also deleted in hGDF-3. This change of hGDF-3 is supposed to be the result of alternative splicing variation or genetic evolution.

Prior to this invention, no other forms of hGDF3 has been isolated or disclosed.

SUMMARY OF INVENTION

One purpose of the invention is to provide a new polynucleotide which encodes a splice variant of human growth/differentiation factor hGDF3. The splice variant of hGDF3 of the invention is named hGDF3-2.

Another purpose of the invention is to provide a novel protein, which is named hGDF3-2.

Still another purpose of the invention is to provide a new method for preparing said new hGDF3-2 protein by recombinant techniques.

The invention also relates to the uses of said hGDF3-2 protein and its coding sequence.

In one aspect, the invention provides an isolated DNA molecule, which comprises a nucleotide sequence encoding a polypeptide having human hGDF3-2 protein activity, wherein said nucleotide sequence shares at least 70% homology to the nucleotide sequence of nucleotides 14–1105 in SEQ ID NO: 5, or said nucleotide sequence can hybridize to the nucleotide sequence of nucleotides 14–1105 in SEQ ID NO: 5 under moderate stringency. Preferably, said nucleotide sequence encodes a polypeptide comprising the amino acid sequence of SEQ ID NO: 6. More preferably, the sequence comprises the nucleotide sequence of nucleotides 14–1105 in SEQ ID NO: 5.

Further, the invention provides an isolated hGDF3-2 polypeptide, which comprises a polypeptide having the amino acid sequence of SEQ ID NO: 6, its active fragments, and its active derivatives. Preferably, the polypeptide is a polypeptide having the amino acid sequence of SEQ ID NO: 6.

The invention also provides a vector comprising said isolated DNA.

The invention further provides a host cell transformed with said vector.

In another aspect, the invention provides a method for producing a polypeptide with the activity of hGDF3-2 protein, which comprises:

(a) forming a hGDF3-2 protein expression vector comprising the nucleotide sequence encoding the polypeptide having the activity of hGDF3-2 protein, wherein said nucleotide sequence is operably linked with an expression regulatory sequences, and said nucleotide sequence shares at least 70% homology to the nucleotide sequence of positions 14–1105 in SEQ ID NO: 5;

(b) introducing the vector of step (a) into a host cell, thereby forming a recombinant cell of hGDF3-2 protein;

(c) culturing the recombinant cell of step (b) under the conditions suitable for the expression of hGDF3-2 polypeptides;

(d) isolating the polypeptides having the activity of hGDF3-2 protein.

In one embodiment of the present invention, the isolated polynucleotide has a full length of 1141 nucleotides, whose detailed sequence is shown in SEQ ID NO: 5. The open reading frame (ORF) is located at nucleotides 14–1105.

In the present invention, the term "isolated" or "purified" or "substantially pure" DNA refers to a DNA or fragment which has been isolated from the sequences which frank it in a naturally occurring state. The term also applies to DNA or DNA fragment which has been isolated from other components naturally accompanying the nucleic acid and from proteins naturally accompanying it in the cell.

In the present invention, the term "hGDF3-2 protein encoding sequence" or "hGDF3-2 polypeptide encoding sequence" refers to a nucleotide sequence encoding a polypeptide having the activity of hGDF3-2 protein, such as the nucleotide sequence of positions 14–1105 in SEQ ID NO: 5 or its degenerate sequence. The degenerate sequences means the sequences formed by replacing one or more codons in the ORF of 14–1105 in SEQ ID NO: 5 with degenerate codes which encode the same amino acid. Because of the degeneracy of codon, the sequence having a homology as low as about 70% to the sequence of nucleotides 14–1105 in SEQ ID NO: 5 can also encode the sequence shown in SEQ ID NO: 6. The term also refers to the nucleotide sequences that hybridize to the nucleotide sequence of nucleotides 14–1105 in SEQ ID NO: 5 under moderate stringency or preferably under high stringency. In addition, the term also refers to the sequences having a homology of at least 70%, preferably 80%, more preferably 90% to the nucleotide sequence of nucleotides 14–1105 in SEQ ID NO: 5.

The term also refers to variants of the sequence in SEQ ID NO: 5, which are capable of encoding a protein having the same function as human hGDF3-2 protein. These variant's includes, but are not limited to, deletions, insertions and/or substitutions of several nucleotides (typically 1–90, preferably 1–60, more preferably 1–20, and most preferably 1–10) and additions of several nucleotides (typically less than 60, preferably 30, more preferably 10, most preferably 5) at 5' end and/or 3' end.

In the present invention, "substantially pure" proteins or polypeptides refers to those which occupy at least 20%, preferably at least 50%, more preferably at least 80%, most preferably at least 90% of the total sample material (by wet weight or dry weight). Purity can be measured by any appropriate method, e.g., in the case of polypeptides by column chromatography, PAGE or HPLC analysis. A substantially purified polypeptides is essentially free of naturally associated components.

In the present invention, the term "hGDF3-2 polypeptide" or "hGDF3-2 protein" refers to a polypeptide having the activity of hGDF3-2 protein comprising the amino acid sequence of SEQ ID NO: 6. The term also comprises the variants of said amino acid sequence which have the same function of human hGDF3-2. These variants include, but are not limited to, deletions, insertions and/or substitutions of several amino acids (typically 1–50, preferably 1–30, more preferably 1–20, most preferably 1–10), and addition of one or more amino acids (typically less than 20, preferably less than 10, more preferably less than 5) at C-terminal and/or N-terminal. For example, the protein functions are usually unchanged when an amino residue is substituted by a similar or analogous one. Further, the addition of one or several amino acids at C-terminal and/or N-terminal will not change the function of protein. The term also includes the active fragments and derivatives of hGDF3-2 protein.

The variants of polypeptide include homologous sequences, allelic variants, natural mutants, induced mutants, proteins encoded by DNA which hybridizes to hGDF3-2 DNA under high or low stringency conditions as well as the polypeptides or proteins retrieved by antisera raised against hGDF3-2 polypeptide. The present invention also provides other polypeptides, e.g., fusion proteins, which include the hGDF3-2 polypeptide or fragments thereof. In addition to substantially full-length polypeptide, the soluble fragments of hGDF3-2 polypeptide are also included. Generally, these fragments comprise at least 10, typically at least 30, preferably at least 50, more preferably at least 80, most preferably at least 100 consecutive amino acids of hGDF3-2 polypeptide.

The present invention also provides the analogues of hGDF3-2 protein or polypeptide. Analogues can differ from naturally occurring hGDF3-2 polypeptide by amino acid sequence differences or by modifications which do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids (e.g., D-amino acids) or non-naturally occurring or synthetic amino acids (e.g., beta- or gamma-amino acids). It is understood that the polypeptides of the invention are not limited to the representative polypeptides listed hereinabove.

Modifications (which do not normally alter primary sequence) include in vivo, or in vitro chemical derivation of polypeptides, e.g., acelylation, or carboxylation. Also included are modifications of glycosylation, e.g., those made by modifying the glycosylation patterns of a polypeptide during its synthesis and processing or in the further processing steps, e.g., by exposing the polypeptide to enzymes which affect glycosylation (e.g., mammalian glycosylating or deglycosylating enzymes). Also included are sequences which have phosphorylated amino acid residues, e.g., phosphotyrosine, phosphoserine, phosphothronine, as well as sequences which have been modified to improve their resistance to proteolytic degradation or to optimize solubility properties.

The invention also includes antisense sequence of the sequence encoding hGDF3-2 polypeptide. Said antisense sequence can be used to inhibit expression of hGDF3-2 in cells.

The invention also includes probes, typically having 8–100, preferably 15–50 consecutive nucleotides. These probes can be used to detect the presence of nucleic acid molecules coding for hGDF3-2 in samples.

The present invention also includes methods for detecting hGDF3-2 nucleotide sequences, which comprises hybridizing said probes to samples, and detecting the binding of the probes. Preferably, the samples are products of PCR amplification. The primers in PCR amplification correspond to coding sequence of hGDF3-2 polypeptide and are located at both ends or in the middle of the coding sequence. In general, the length of the primers is 20 to 50 nucleotides.

A variety of vectors known in the art, such as those commercially available, are useful in the invention.

In the invention, the term "host cells" includes prokaryotic and eukaryotic cells. The common prokaryotic host cells include *Escherichi coli, Bacillus subtilis*, and so on. The common eukaryotic host cells include yeast cells, insect cells, and mammalian cells. Preferably, the host cells are eukaryotic cells, e.g., CHO cells, COS cells, and the like.

In another aspect, the invention also includes antibodies, preferably monoclonal antibodies, which are specific for polypeptides encoded by hGDF3-2 DNA or fragments thereof. By "specificity", it is meant an antibody which binds to the hGDF3-2 gene products or a fragments thereof. Preferably, the antibody binds to the hGDF3-2 gene products or a fragments thereof and does not substantially recognize nor bind to other antigenically unrelated molecules. Antibodies which bind to hGDF3-2 and block hGDF3-2 protein and those which do not affect the hGDF3-2 function are included in the invention. The invention also includes antibodies which bind to the hGDF3-2 gene product in its unmodified as well as modified form.

The present invention includes not only intact monoclonal or polyclonal antibodies, but also immunologically-active antibody fragments, e.g., a Fab' or (Fab)$_2$ fragment, an antibody light chain, an antibody heavy chain, a genetically engineered single chain Fv molecule (Lander, et al., U.S. Pat. No. 4,946,778), or a chimeric antibody, e.g., an antibody which contains the binding specificity of a murine antibody, but the remaining portion of which is of human origin.

The antibodies in the present invention can be prepared by various techniques known to those skilled in the art. For example, purified hGDF3-2 gene products, or its antigenic fragments can be administrated to animals to induce the production of polyclonal antibodies. Similarly, cells expressing hGDF3-2 or its antigenic fragments can be used to immunize animals to produce antibodies. Antibodies of the invention can be monoclonal antibodies which can be prepared by using hybridoma technique (See Kohler, et al., Nature, 256; 495,1975; Kohler, et al., Eur. J. Immunol. 6: 511,1976; Kohler, et al., Eur. J. Immunol. 6: 292, 1976; Hammerling, et al., In Monoclonal Antibodies and T Cell Hybridomas, Elsevier, N.Y., 1981). Antibodies of the invention comprise those which block hGDF3-2 function and those which do not affect hGDF3-2 function. Antibodies in the invention can be produced by routine immunology techniques and using fragments or functional regions of hGDF3-2 gene product. These fragments and functional regions can be prepared by recombinant methods or synthesized by a polypeptide synthesizer. Antibodies binding to unmodified hGDF3-2 gene product can be produced by immunizing animals with gene products produced by prokaryotic cells (e.g., *E. coli*); antibodies binding to post-translationally modified forms thereof can be acquired by immunizing animals with gene products produced by eukaryotic cells (e.g., yeast or insect cells).

The full length human hGDF3-2 nucleotide sequence or its fragment of the invention can be prepared by PCR amplification, recombinant method and synthetic method. For PCR amplification, one can obtain said sequences by designing primers based on the nucleotide sequence disclosed in the invention, especially the sequence of ORF, and using cDNA library commercially available or prepared by routine techniques known in the art as a template. When the sequence is long, it is usually necessary to perform two or more PCR amplifications and link the amplified fragments together in the correct order.

Once the sequence is obtained, a great amount of the sequences can be produced by recombinant methods. Usually, said sequence is cloned in a vector which is then transformed into a host cell. Then the sequence is isolated from the amplified host cells using conventional techniques.

Further, the sequence can be produced by synthesis. Typically, several small fragments are synthesized and linked together to obtain a long sequence. At present, it is completely feasible to chemically synthesize the DNA sequence encoding the protein of the invention, or the fragments or derivatives thereof. In addition, the mutation can be introduced into the sequence of the protein by chemical synthesis.

In addition to recombinant techniques, the protein fragments of the invention may also be prepared by direct chemical synthesis using solid phase synthesis techniques (Stewart et al., (1969) Solid-Phase Peptide 20 Synthesis, WH Freeman Co., San Francisco; Merrifield J. (1963), J. Am. Chem. Assoc. 85: 2149–2154). In vitro protein synthesis can be performed manually or automatically, e.g., using a Model 431 Peptide Synthesizer (Applied Biosystems, Foster City, Calif.). The fragments of protein of the invention can be synthesized separately and linked together using chemical methods so as to produce full-length molecule.

The sequences encoding the protein of the present invention are also valuable for gene mapping. For example, the accurate chromosome mapping can be performed by hybridizing cDNA clones to a chromosome in metaphase. This technique can use cDNA as short as about 500 bp, or as long as about 2000 bp, or more. For details, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found in, e.g., Mendelian Inheritance in Man (available on-line through Johns Hopkins: University Welch Medical Library). The relationships between genes and diseases that have been mapped to the same chromosomal region are then identified through linkage analysis.

Then, the differences in the cDNA or genomic sequence between affected and unaffected individuals can also be determined. If a mutation is observed in some or all of the affected individuals but not in any normal individual, then the mutation is likely to be the causative agent of the disease.

The substances which act with the hGDF3-2, e.g., receptors, inhibitors and antagonists, can be screened out by various conventional techniques, using the protein of the invention.

The protein, antibody, inhibitor, antagonist or receptor of the invention provide different effects when administrated in therapy. Usually, these substances are formulated with a non-toxic, inert and pharmaceutically acceptable aqueous carrier. The pH typically ranges from 5 to 8, preferably from about 6 to 8, although pH may alter according to the property of the formulated substances and the diseases to be treated.

The formulated pharmaceutical composition is administrated in conventional routine including, but not limited to, intramuscular, intraperitoneal, subcutaneous, intracutaneous, or topical administration.

As an example, the human hGDF3-2 protein of the invention may be administrated together with the suitable and pharmaceutically acceptable carrier. The examples of carriers include, but are not limited to, saline, buffer solution, glucose, water, glycerin, ethanol, or the combination thereof. The pharmaceutical formulation should be suitable for the delivery method. The human hGDF3-2 protein of the invention may be in the form of injections which are made by conventional methods, using physiological saline or other aqueous solution containing glucose or auxiliary substances. The pharmaceutical compositions in the form of tablet or capsule may be prepared by routine methods. The pharmaceutical compositions, e.g., injections, solutions, tablets, and capsules, should be manufactured under sterile conditions. The active ingredient is administrated in therapeutically effective amount, e.g., from about 1ug to 5 mg per kg body weight per day. Moreover, the polypeptide of the invention can be administrated together with other therapeutic agent.

When the human hGDF3-2 polypeptides of the invention are used as a pharmaceutical, the therapeutically effective amount of the polypeptides are administrated to mammals. Typically, the therapeutically effective amount is at least about 10 ug/kg body weight and less than about 8 mg/kg body weight in most cases, and preferably about 10 ug–1 mg/kg body weight. Of course, the precise amount will depend upon various factors, such as delivery methods, the subject health, and the like, and is within the judgment of the skilled clinician.

DESCRIPTION OF DRAWINGS

FIG. 1 shows an alignment comparison of amino acid sequences of hGDF3-2 (SEQ ID NO: 6) of the invention and murine GDF3 (SEQ ID NO: 12) and human GDF3 (hGDF3) (SEQ ID NO: 11). The identical and similar amino acids are indicated by ":" and "." between the sequences, respectively.

In one embodiment, the cDNA sequence of HGDF3-2 was obtained as follows: human bone marrow λgt 11 cDNA library (Clontech) was used as a template and the forward primer A1:5'-GGAGCTCTCCCCGGTCTGAC-3'(SEQ ID NO 1), A2:5'-CACTCCAGAGGCCATGCTTGG-3'(SEQ ID NO: 2), and reverse primers B1:5'-CCTAAGAACACTCCTTCTATTCC-3'(SEQ ID NO: 3), B2:5'-CTAAGTGGTCATAAACCAGATTAGG-3'(SEQ ID NO: 4) were synthesized. Primers A1, B2 were first used to amplify the cDNA library of human bone marrow. Then an additional PCR was carried out with primers A2 and B1, using the amplified product as a template. Target fragments of 1141 bp were obtained. The sequencing of the PCR product gave the full length cDNA Sequence shown in SEQ ID NO: 5.

Homology comparison showed that the nucleotide sequence and the coded protein sequence of the invention shared remarkable homology to murine GDF3. Noticeably, it is completely consistent with the human GDF-3 (hGDF3) except the 5' end, and the only difference is that the encoded proteins have different lengths of N-terminal. However, hGDF3-2 shares higher homology to murine GDF-3. According to the expression pattern in the tissues, hGDF3-2 is supposed to be related to lymphocytopoiesis, erythropoiesis and embryonic development of skeleton and cartilage. Moreover, the specific expression of hGDF3 in the embryonal carcinoma (EC) stem cells indicates it may be used as a molecular marker for EC cells and may play a role in the formation and maintenance of EC stem cells.

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLES

Example 1

The cloning and sequencing of hGDF3-2 cDNA sequence
1. Amplification With Primers The template was human bone marrow λgt 11 cDNA library (commercially available from Clontech). The PCR were carried out with two pairs of primers: forward primers A1: 5'-GGAGCTCTCC CCGGTCTGAC-3' (SEQ ID NO:1), and A2:5'-CACTCCAGAGGCCATGCTTCG-3' (SEQ ID NO:2); reverse primers B1:5'-CCTAAGAACACTCCTTCTATTCC-3' (SEQ ID NO:3), and B2:5'-CTAAGTGGTCATAAACCAGATTAGG-3' (SEQ ID NO:4). Firstly, PCR was carried out using primers A1 and B2. The PCR condition was 4 mins at 93° C.; followed by 35 cycles with 1 min at 93° C., 1 min at 66° C., and 1 min at 72° C.; and, finally 5 mins at 72° C. Then, using the above PCR product as a template, an additional PCR was carried out with primers A2 and B1. The PCR condition was 4 mins at 93° C; followed by 35 cycles with 1 min at 93° C., 1 min at 64° C., and 1 min at 72° C.; and, finally, 5 mins at 72° C. The A2-B1 PCR fragments were detected by electrophoresis. The target fragment was 1141 bp.
2. Sequencing PCR Products PCR products amplified by primers A2 and B1 were linked with pGEM-T™ vector (Promega) and transformed into E. coli JM103. The plasmids were extracted using QIAprep Plasmid Kit (QIAGEN). The oriented serial deletion of the inserted fragments was carried out with Double-Stranded Nested Deletion Kit (Pharmacia), and the deletants were quickly identified by PCR and arranged in order. The deletants successively cut-off were sequenced with SequiTherm EXCEL™ DNA Sequencing Kit (Epicentre Technologies). A full length cDNA sequence of 1141 bp was obtained by overlapping the sequences with computer software. The detailed sequence is shown in SEQ ID NO: 5 with an open reading frame (ORF) located at nucleotides 14–1105.

According to the resultant full-length cDNA sequence, the amino acid sequence of hGDF3-2 was deduced, having 363 amino acid residues totally. See SEQ ID NO: 6 for its amino acid sequence in details.

Example 2

Homologous comparison

First, the conservative sequence of TGF-β superfamily is found in the sequence of hGDF3-2 protein:

(L/I/V/M)$X_2$P$X_2$(F/Y)$X_4$CXGXC (SEQ ID NO:10) wherein (L/I/V/M) represents any amino acid of L, I, V, and M; $X_2$ represents for any two amino acids. The sequence corresponding to the conservative sequence in hGDF3-2 is: $_{281}$IIAPKGFMANYCHGEC$_{296}$.(SEQ ID NO: 13)

The full length cDNA sequence of hGDF3-2 and the coded protein were used for homologous searching Non-redundant GenBank+EMBL+DDBJ+PDB and on-redundant GenBank CDS translations +PDB+ SwissProt+Spupdate+PIR databases by BLAST algorithm. The result showed that they shared high homology to murine GDF3 and human hGDF3. On the protein level, the amino acid sequence of hGDF3-2 shares 69.1% identity and 76.5% similarity with GDF3, when analyzed by PCGENE software. Furthermore, hGDF3-2 was identical to hGDF3 except that hGDF3-2 had nearly 50 additional amino acid residues at N-terminal. The relationship of the three proteins is shown in FIG. 1. Based on the homology between GDF-3, hGDF3 and hGDF3-2 and the length of the proteins, it is strongly suggested that hGDF3-2 and hGDF3 are encoded by the same gene, and the difference is resulted from the different splicing of said gene. Moreover, it is reasonable to state that hGDF3-2, instead of hGDF3, is the real human homologous gene for mice GDF-3. Therefore, hGDF3-2 performs many functions identical to or similar to those of GDF-3 or hGDF3.

The transcripts of GDF-3 gene were found only in a few tissues, e.g., thymus, spleen, bone marrow, etc., in adult mice, which suggested GDF-3 may function in lymphocytopoiesis and erythropoiesis (J. Biol. Chem., 1993, 268(5), 3444–3449). Jones found that GDF-3 expressed in skeletal and cartilaginous tissues embryos during the gestation, which indicated that GDF-3 might be involved in the skeletal development as well (Mol. Endo., 1992, 6, 1961–1968). Similarly, the expression of hGDF3 was also tissue specific (Oncogene, 1998, 16, 95–103).

Further, GDF-3 and hGDF3 were also expressed specifically in EC stem cells. Studies have shown that, regardless of their differentiation ability or nutritional dependence of the cell strains, it was easy to detect the transcript of hGDF3 in all of the tested EC cell strains. Retinoic acid could induce cellular differentiation. Interestingly, the expression amount of hGDF3 in pluripotent EC cells drop to a very low level after a long time treatment of retinoic acid. However, the treatment of retinoic acid did not lead to a decreased hGDF3 expression in nullipotent EC cell strains. Therefore, the expression of hGDF3 in human EC cell strains was directly related to the phenotype of EC stem cells. Other reports demonstrated that the expression of hGDF3 was EC-cell specific, suggesting that hGDF3 might be a molecular marker of EC cells. This property can be used to identify and screen particular cell types. Noticeably, hGDF3 is located in human chromosome 12p, which is a focused area because of the overexpression in CIS (carcinoma in situ), TGCT and TGCT derivative cell strains. Summing up, although the biological meaning of the association of GDF-3 and EC cells is still unclear, the above phenomena reasonably suggest that hGDF3 functions in the formation and maintenance of EC stem cells (Oncogene, 1998, 16, 95–103).

The hGDF3-2 of the invention can be used not only as a member of the superfamily in the study of function, but also to produce fusion proteins with other proteins, such as immunoglobulins. Besides, hGDF3-2 can be fused with or exchange fragments with other members of the superfamily to form new proteins. For example, the N terminal of hGDF3-2 can exchange with the N terminal of hGDF3 or mice GDF-3 to produce proteins which are more active or have new properties.

The antibodies against hGDF3-2 can be used to screen other members of the superfamily or to purify the related proteins such as other members of the superfamily through affinity purification.

Example 3
Expression of hGDF3-2 in *E. coli*

In this example, the cDNA sequence encoding hGDF3-2 (GenBank Accession No. AF064257. The gene sequence was not available to the public prior to the filing of the application because of the secrecy protection.) was amplified with oligonucleotide PCR primers corresponding to 5'- and 3'-end of said DNA sequence. The resultant hGDF3-2 cDNA was used as an insertion fragment.

The sequence of 5'-end oligonucleotide primer was:
5'-ATACGGATCCATGCTTCGTTTCTTGCCAG-3' (SEQ ID NO: 7).

This primer contained a cleavage site of restriction endonuclease BamH I, followed by 19 nucleotides of hGDF3-2 coding sequence starting from the start codon.

The sequence of 3'-end primer was:
5'-GTTAGTCGACCTACCCACACCCACATTCAT-3' (SEQ ID NO: 8).

This primer contained a cleavage site of restriction endonuclease SalI, a translation terminator and partial hGDF3-2 coding sequence.

These cleavage sites of restriction endonuclease in primers corresponded to the cleavage sites in bacterial expression vector pQE-9 (Qiagen Inc., Chatsworth, Calif.). Vector pQE-9 encodes an antibiotic resistance ($Amp^r$), a bacterial replication origin (ori), an IPTG-adjustable promotor/operon (P/O), a ribosome-binding site (RBS), a six-hisitine tag (6-His) and cloning sites of restriction endonuclease.

Vector pQE-9 and insertion fragments were digested by BamHI and SalI, and then linked together, ensuring that the open reading frame started from the bacterial RBS. Then, the linkage mixture was used to transform *E.coli* M15/rep4 (Qiagen) containing multi-copy of plasmid pREP4 which expressed repressor of lacI and was resistant to kanamycin ($Kan^r$). Transformants were screened out in LB medium containing Amp and Kan. The plasmids were extracted. The size and direction of the inserted fragments were verified by BamHI digestion. The sequencing confirmed that hGDF3-2 cDNA fragment was correctly inserted into the vector.

The positive clones of transformant were cultured overnight in LB liquid medium supplemented with Amp (100 ug/ml) and Kan (25 ug/ml). The overnight culture was 1:100–1:250 diluted, inoculated into large volume medium, and cultured until the 600 nm optical density ($OD_{600}$) reached 0.4–0.6. IPTG (isopropylthio-beta-D-galactoside) was added to final concentration of 1 mM. By deactivating repressor of LacI, IPTG induced and promoted P/O, thereby increasing the expression of gene. The cells were cultured for another 3–4 hours, and then centrifuged (6000×g, 20 mins). The cultures were sonicated, and cell lysate was collected and diluted with 6M guanidine hydrochloride. After clarification, the dissolved hGDF3-2 in solution were purified by nickel-chelated column chromatography under the conditions suitable for the tight binding of 6-His tagged protein and column. hGDF3-2 was eluted with 6M guanidine hydrochloride (pH 5.0). The denaturalized proteins in guanidine hydrochloride were precipitated by several methods. First, guanidine hydrochloride was separated by dialysis. Alternatively, the purified protein, which was isolated from nickel-chelated column, bound to the second column with decreased linear gradient of guanidine hydrochloride. The proteins were denatured when binding to the column. Then, the proteins were eluted with guanidine hydrochloride (pH 5.0). Finally, the soluble proteins were dialyzed with PBS, then preserved in glycerol stock solution with the final glycerol concentration of 10% (w/v).

The molecular weight of the expressed protein was about 41 kDa, as identified by 12% SDS-PAGE.

Moreover, the sequencing results of the 10 amino acids at the N- and C-terminal of the expressed protein indicated that they were identical to those in SEQ ID NO: 6.

Example 4

Expression of hGDF3-2 in eukaryotic cells (CHO cell line)

In this example, the cDNA sequence encoding hGDF3-2 (GenBank Accession No. AF064257) was amplified with oligonucleotide PCR primers corresponding to 5'- and 3'-end of said DNA sequence. The resultant product was used as an insertion fragment.

The sequence of 5'-end oligonucleotide primer was:

5'-ATACGGATCCATGCTTCGTTTCTTGCCAG -3' (SEQ ID NO: 7),

This primer contained a cleavage site of restriction endonuclease BamHI, followed by 19 nucleotides of hGDF3-2 coding sequence starting from the start codon.

The sequence of 3'-end primer was:

5'-GTTAGAATTCCTACCCACACCCACATTCAT-3' (SEQ ID NO: 9)

This primer contained a cleavage site of restriction endonuclease EcoRI, a translation stop codon, and partial hGDF3-2 coding sequence.

These cleavage sites of restriction endonuclease in primers corresponded to the cleavage sites in expression vector pcDNA3 for CHO cell. This vector encoded two kinds of antibiotic resistance (Amp$^r$ and Neo$^r$), a phage replication origin (f1 ori), a virus replication origin (SV40 ori), a T7 promoter, a virus promoter (P-CMV), a Sp6 promoter, a polyadenylation signal of SV40 and the corresponding polyA sequence thereof, a polyadenylation signal of BGH and the corresponding poly A sequence thereof.

The vector pcDNA3 and insertion fragment were digested with BamHI and EcoRI, and linked together. Subsequently, E.coli strand DH5 α was transformed with linkage mixture. Transformants were screened out in LB medium containing Amp. The clones containing the needed constructs were cultured overnight in LB liquid medium supplemented with Amp (100 ug/ml). Plasmids were extracted. The size and direction of the inserted fragments were verified by PstI digestion. The sequencing indicated that hGDF3-2 cDNA fragment was correctly inserted into the vector.

Plasmids were transfected into CHO cells by lipofection with Lipofectin Kit (GIBco Life). After transfecting the cells for 48 hours and screening the cells with G418 for 2–3 weeks, the cells and cell supernatant were collected and the activity of the expressed protein was measured. G418 was removed and the transformants were subcultured continuously. The mixed clonal cells were limiting diluted and the subclones with higher protein activity were selected. The positive subclones were mass cultured by routine methods. 48 hours later, the cells and supernatant were collected. The cells were ultrasonicated. Using 50 mM Tris-HCl (pH7.6) solution containing 0.05% Triton as an equilibrium solution and eluent, the active peek of the protein was collected with a pre-balanced Superdex G-75 column. Then, using 50 mM Tris-HCl (pH8.0) solution containing 0–1 M NaCl as an eluent, the protein was gradiently washed on a DEAE-Sepharose column balanced with 50 mM Tris-HCl (pH8.0) solution. The active peek of the protein was collected. The solution of the expressed protein was dialyzed with PBS (pH7.4), and finally lyophilized and preserved.

The molecular weight of the expressed protein was about 41 kDa as identified by 12% SDS-PAGE.

Moreover, the sequencing results of the 10 amino acids at the N- and C-terminal of the expressed protein indicated that they were identical to those in SEQ ID NO: 6.

Example 5

Antibody Preparation

Antibodies were produced by immunizing animals with the recombinant proteins obtained in Examples 3 or 4. The method was as follows: the recombinant proteins were isolated by chromatography, and stored for use. Alternatively, the protein was isolated by SDS-PAGE electrophoresis, and obtained by cutting eletrophoretic bands from gel. The protein was emulsified with Freund's complete adjuvant of the same volume. The emulsified protein was injected intraperitoneally into mice at a dosage of 50–100 ug/0.2 ml. 14 days later, the same antigen was emulsified with Freund's incomplete adjuvant and injected intraperitoneally into mice at a dosage of 50–100 ug/0.2 ml for booster immunization. Booster immunization was carried out every 14 days, for at least three times. The specific activity of the obtained antiserum was evaluated by its ability of precipitating the translation product of hGDF3-2 gene in vitro.

All the documents cited herein are incorporated into the invention as reference, as if each of them is individually incorporated. Further, it is appreciated that, in the above teaching of the invention, the skilled in the art can make certain changes or modifications to the invention, and these equivalents are still within the scope of the invention defined by the appended claims of the present application.

What is claimed is:

1. An isolated DNA molecule comprising a nucleotide sequence encoding a polypeptide comprising the amino acid sequence of SEQ ID NO: 6.

2. The DNA molecule of claim 1 wherein said nucleotide sequence comprises the nucleotide sequence of nucleotides 14–1105 in SEQ ID NO: 5.

3. A vector containing the DNA sequence of claim 1.

4. A host cell transformed by the vector of claim 3.

5. The host cell of claim 4 which is *E.coli.*

6. The host cell of claim 4 which is a eukaryotic cell.

7. A method for producing a hGDF3-2 protein, which comprises the steps of;

(a) forming an expression vector of hGDF3-2 protein comprising the nucleotide sequence encoding the hGDF3-2 protein having the amino acid sequence of SEQ ID NO: 6, wherein said nucleotide sequence is operably linked with an expression regulatory sequence;

(b) introducing the vector of step (a) into a host cell, thereby forming a recombinant cell of hGDF3-2 protein;

(c) culturing the recombinant cell of step (b) under conditions suitable for expression of hGDF3-2 protein;

(d) isolating the hGDF3-2 protein.

8. An isolated hGDF3-2 protein comprising a polypeptide having the amino acid sequence of SEQ ID NO:6.

* * * * *

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
ggagctctcc ccggtctgac                                          20

<210> SEQ ID NO 2
<211> LENGTH: 21
```

-continued

```
<212> TYPE: DNA
<213> ORGANISM: Artificial Sequence
<220> FEATURE:
<223> OTHER INFORMATION: Oligonucleotide

<400> SEQUENCE: 2
cactccagag gccatgcttc g                                          21

<210> SEQ ID NO 3
<211> LENGTH: 23
<212> TYPE: DNA
<213> ORGANISM: Artificial Sequence
<220> FEATURE:
<223> OTHER INFORMATION: Oligonucleotide

<400> SEQUENCE: 3
cctaagaaca ctccttctat tcc                                        23

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide

<400> SEQUENCE: 4
ctaagtggtc ataaaccaga ttagg                                      25

<210> SEQ ID NO 5
<211> LENGTH: 1141
<212> TYPE: DNA
<213> ORGANISM: Homo sapiens

<400> SEQUENCE: 5
cactccagac gccatgcttc gtttcttgcc agatttggct ttcagcttcc tgttaattct    60
ggctttgggc caggcagtcc aatttcaaga atatgtcttt ctccaatttc tgggcttaga   120
taaggcgcct tcaccccaca agttccaacc tgtgccttat atcttgaaga aaattttcca   180
ggatcgcgag gcagcggcga ccactggggt ctcccgagac ttatgctacg taaggagct    240
gggcgtccgc gggaatgtac ttcgctttct cccagaccaa ggtttctttc tttacccaaa   300
gaaaatttcc caagcttcct cctgcctgca gaagctcctc tactttaacc tgtctgccat   360
caaagaaagg gaacagctga cattggccca gctggtggac ttggggccca attcttacta   420
taacctggga ccagagctgg aactggctct gttcctggtt caggagcctc atgtgtggcg   480
ccagaccacc cctaagccag gtaaaatgtt tgtgttgcgg tcagtcccat ggccacaagg   540
tgctgttcac ttcagcctgc tggatgtagc taaggattgg aatgacaacc cccggaaaaa   600
tttcgggtta ttcctggaga tactggtcaa agaaaataga gactcagggg tgaattttca   660
gcctgaagac acctgtgcca gactaagatg ctccccttcat gcttccctgc tggtggtgac   720
tctcaaccct gatcagtgcc acccttctcg gaaaaggaga gcagccatcc ctgtccccaa   780
gctttcttgt aagaacctct gccaccgtca ccagctattc attaacttcc gggacctggg   840
ttggcacaag tggatcattg ccccccaaggg tttcatggca aattactgcc atggagagtg   900
tcccttctca ctgaccatct ctctcaacag ctccaattat gctttcatgc aagccctgat   960
gcatgccgtt gacccagaga tcccccaggc tgtgtgtatc cccaccaagc tgtctcccat  1020
ttccatgctc taccaggaca ataatgacaa tgtcattcta cgacattatg aagacatggt  1080
agtcgatgaa tgtgggtgtg ggtaggatgt cagaaatggg aatagaagga gtgttcttag  1140
``` g    1141

<210> SEQ ID NO 6
<211> LENGTH: 363
<212> TYPE: PRT
<213> ORGANISM: Homo sapiens

<400> SEQUENCE: 6

Met Leu Arg Phe Leu Pro Asp Leu Ala Phe Ser Phe Leu Leu Ile Leu
1               5                   10                  15

Ala Leu Gly Gln Ala Val Gln Phe Gln Glu Tyr Val Phe Leu Gln Phe
            20                  25                  30

Leu Gly Leu Asp Lys Ala Pro Ser Pro His Lys Phe Gln Pro Val Pro
        35                  40                  45

Tyr Ile Leu Lys Lys Ile Phe Gln Asp Arg Glu Ala Ala Thr Thr
    50                  55                  60

Gly Val Ser Arg Asp Leu Cys Tyr Val Lys Glu Leu Gly Val Arg Gly
65                  70                  75                  80

Asn Val Leu Arg Phe Leu Pro Asp Gln Gly Phe Phe Leu Tyr Pro Lys
                85                  90                  95

Lys Ile Ser Gln Ala Ser Ser Cys Leu Gln Lys Leu Leu Tyr Phe Asn
            100                 105                 110

Leu Ser Ala Ile Lys Glu Arg Glu Gln Leu Thr Leu Ala Gln Leu Val
        115                 120                 125

Asp Leu Gly Pro Asn Ser Tyr Tyr Asn Leu Gly Pro Glu Leu Glu Leu
    130                 135                 140

Ala Leu Phe Leu Val Gln Glu Pro His Val Trp Arg Gln Thr Thr Pro
145                 150                 155                 160

Lys Pro Gly Lys Met Phe Val Leu Arg Ser Val Pro Trp Pro Gln Gly
                165                 170                 175

Ala Val His Phe Ser Leu Leu Asp Val Ala Lys Asp Trp Asn Asp Asn
            180                 185                 190

Pro Arg Lys Asn Phe Gly Leu Phe Leu Glu Ile Leu Val Lys Glu Asn
        195                 200                 205

Arg Asp Ser Gly Val Asn Phe Gln Pro Glu Asp Thr Cys Ala Arg Leu
    210                 215                 220

Arg Cys Ser Leu His Ala Ser Leu Leu Val Val Thr Leu Asn Pro Asp
225                 230                 235                 240

Gln Cys His Pro Ser Arg Lys Arg Arg Ala Ala Ile Pro Val Pro Lys
                245                 250                 255

Leu Ser Cys Lys Asn Leu Cys His Arg His Gln Leu Phe Ile Asn Phe
            260                 265                 270

Arg Asp Leu Gly Trp His Lys Trp Ile Ile Ala Pro Lys Gly Phe Met
        275                 280                 285

Ala Asn Tyr Cys His Gly Glu Cys Pro Phe Ser Leu Thr Ile Ser Leu
    290                 295                 300

Asn Ser Ser Asn Tyr Ala Phe Met Gln Ala Leu Met His Ala Val Asp
305                 310                 315                 320

Pro Glu Ile Pro Gln Ala Val Cys Ile Pro Thr Lys Leu Ser Pro Ile
                325                 330                 335

Ser Met Leu Tyr Gln Asp Asn Asp Asn Val Ile Leu Arg His Tyr
            340                 345                 350

Glu Asp Met Val Val Asp Glu Cys Gly Cys Gly
        355                 360

-continued

<210> SEQ ID NO 7
<211> LENGTH: 29
<212> TYPE: DNA
<213> ORGANISM: Artificial Sequence
<220> FEATURE:
<223> OTHER INFORMATION: Oligonucleotide

<400> SEQUENCE: 7
atacggatcc atgcttcgtt tcttgccag                29

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide

<400> SEQUENCE: 8
gttagtcgac ctacccacac ccacattcat                30

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide

<400> SEQUENCE: 9
gttagaattc ctacccacac ccacattcat                30

<210> SEQ ID NO 10
<211> LENGTH: 16
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: Conservative sequence of TGF-beta superfamily
<220> FEATURE:
<221> NAME/KEY: MISC_FEATURE
<222> LOCATION: (13)..(13)
<223> OTHER INFORMATION: Conservative sequence of TGF-beta superfamily
<220> FEATURE:
<221> NAME/KEY: MISC_FEATURE
<222> LOCATION: (15)..(15)
<223> OTHER INFORMATION: Conservative sequence of TGF-beta superfamily

<400> SEQUENCE: 10

Xaa Xaa Xaa Pro Xaa Xaa Xaa Xaa Xaa Xaa Xaa Cys Xaa Gly Xaa Cys
1               5                  10                  15

<210> SEQ ID NO 11
<211> LENGTH: 313
<212> TYPE: PRT
<213> ORGANISM: Homo sapiens

<400> SEQUENCE: 11

Met Lys Glu Ile Ser Gln Asp Arg Glu Ala Ala Thr Thr Gly Val
1               5                  10                  15

Ser Arg Asp Leu Cys Tyr Val Lys Glu Leu Gly Val Arg Gly Asn Val
                20                  25                  30

Leu Arg Phe Leu Pro Asp Gln Gly Phe Phe Leu Tyr Pro Lys Lys Ile
            35                  40                  45

Ser Gln Ala Ser Ser Cys Leu Gln Lys Leu Leu Tyr Phe Asn Leu Ser
        50                  55                  60

```
Ala Ile Lys Glu Arg Glu Gln Leu Thr Leu Ala Gln Leu Val Asp Leu
 65                  70                  75                  80

Gly Pro Asn Ser Tyr Tyr Asn Leu Gly Pro Glu Leu Glu Leu Ala Leu
                 85                  90                  95

Phe Leu Val Gln Glu Pro His Val Trp Arg Gln Thr Thr Pro Lys Pro
            100                 105                 110

Gly Lys Met Phe Val Leu Arg Ser Val Pro Trp Pro Gln Gly Ala Val
            115                 120                 125

His Phe Ser Leu Leu Asp Val Ala Lys Asp Trp Asn Asp Asn Pro Arg
130                 135                 140

Lys Asn Phe Gly Leu Phe Leu Glu Ile Leu Val Lys Glu Asn Arg Asp
145                 150                 155                 160

Ser Gly Val Asn Phe Gln Pro Glu Asp Thr Cys Ala Arg Leu Arg Cys
                165                 170                 175

Ser Leu His Ala Ser Leu Leu Val Thr Leu Asn Pro Asp Gln Cys
                180                 185                 190

His Pro Ser Arg Lys Arg Arg Ala Ala Ile Pro Val Pro Lys Leu Ser
                195                 200                 205

Cys Lys Asn Leu Cys His Arg His Gln Leu Phe Ile Asn Phe Arg Asp
        210                 215                 220

Leu Gly Trp His Lys Trp Ile Ile Ala Pro Lys Gly Phe Met Ala Asn
225                 230                 235                 240

Tyr Cys His Gly Glu Cys Pro Phe Ser Leu Thr Ile Ser Leu Asn Ser
                245                 250                 255

Ser Asn Tyr Ala Phe Met Gln Ala Leu Met His Ala Val Asp Pro Glu
                260                 265                 270

Ile Pro Gln Ala Val Cys Ile Pro Thr Lys Leu Ser Pro Ile Ser Met
                275                 280                 285

Leu Tyr Gln Asp Asn Asn Asp Asn Val Ile Leu Arg His Tyr Glu Asp
                290                 295                 300

Met Val Val Asp Glu Cys Gly Cys Gly
305                 310

<210> SEQ ID NO 12
<211> LENGTH: 366
<212> TYPE: PRT
<213> ORGANISM: Mus musculus

<400> SEQUENCE: 12

Met Gln Pro Tyr Gln Arg Leu Leu Ala Leu Gly Phe Leu Leu Leu Thr
  1               5                  10                  15

Leu Pro Trp Gly Gln Thr Ser Glu Phe Gln Asp Ser Asp Leu Leu Gln
                 20                  25                  30

Phe Leu Gly Leu Glu Lys Ala Pro Ser Pro His Arg Phe Gln Pro Val
             35                  40                  45

Pro Arg Val Leu Arg Lys Ile Ile Arg Ala Arg Glu Ala Ala Ala Ala
 50                  55                  60

Ser Gly Ala Ser Gln Asp Leu Cys Tyr Val Lys Glu Leu Gly Val Arg
 65                  70                  75                  80

Gly Asn Leu Leu Gln Leu Leu Pro Asp Gln Gly Phe Phe Leu Asn Thr
                 85                  90                  95

Gln Lys Pro Phe Gln Asp Gly Ser Cys Leu Gln Lys Val Leu Tyr Phe
            100                 105                 110

Asn Leu Ser Ala Ile Lys Glu Lys Ala Lys Leu Thr Met Ala Gln Leu
            115                 120                 125
```

-continued

```
Thr Leu Asp Leu Gly Pro Arg Ser Tyr Tyr Asn Leu Arg Pro Glu Leu
    130                 135                 140

Val Val Ala Leu Ser Val Val Gln Asp Arg Gly Val Trp Gly Arg Ser
145                 150                 155                 160

His Pro Lys Val Gly Arg Leu Leu Phe Leu Arg Ser Val Pro Gly Pro
                165                 170                 175

Gln Gly Gln Leu Gln Phe Asn Leu Gln Gly Ala Leu Lys Asp Trp Ser
                180                 185                 190

Ser Asn Arg Leu Lys Asn Leu Asp Leu His Leu Glu Ile Leu Val Lys
            195                 200                 205

Glu Asp Arg Tyr Ser Arg Val Thr Val Gln Pro Glu Asn Pro Cys Asp
        210                 215                 220

Pro Leu Leu Arg Ser Leu His Ala Ser Leu Leu Val Val Thr Leu Asn
225                 230                 235                 240

Pro Lys His Cys His Pro Ser Ser Arg Lys Arg Arg Ala Ala Ile Ser
                245                 250                 255

Val Pro Lys Gly Phe Cys Arg Asn Phe Cys His Arg His Gln Leu Phe
                260                 265                 270

Ile Asn Phe Gln Asp Leu Gly Trp His Lys Trp Val Ile Ala Pro Lys
            275                 280                 285

Gly Phe Met Ala Asn Tyr Cys His Gly Glu Cys Pro Phe Ser Met Thr
    290                 295                 300

Thr Tyr Leu Asn Ser Ser Asn Tyr Ala Phe Met Gln Ala Leu Met His
305                 310                 315                 320

Met Ala Asp Pro Lys Val Pro Lys Ala Val Cys Val Pro Thr Lys Leu
                325                 330                 335

Ser Pro Ile Ser Met Leu Tyr Gln Asp Ser Asp Lys Asn Val Ile Leu
                340                 345                 350

Arg His Tyr Glu Asp Met Val Val Asp Glu Cys Gly Cys Gly
            355                 360                 365

<210> SEQ ID NO 13
<211> LENGTH: 16
<212> TYPE: PRT
<213> ORGANISM: Homo sapiens

<400> SEQUENCE: 13

Ile Ile Ala Pro Lys Gly Phe Met Ala Asn Tyr Cys His Gly Glu Cys
1               5                   10                  15
```